United States Patent
Lacroix et al.

(12) 
(10) Patent No.: US 6,649,560 B2
(45) Date of Patent: Nov. 18, 2003

(54) BULK CATALYSTS BASED ON CHROMIUM AND ON NICKEL FOR THE GAS-PHASE FLUORINATION OF HALOGENATED HYDROCARBONS

(75) Inventors: Eric Lacroix, Amberieux d'Azergues (FR); Jean-Pierre Schirmann, Paris (FR)

(73) Assignee: Elf Atochem, Puteaux (FR)

( * ) Notice: Subject to any disclaimer, the term of this patent is extended or adjusted under 35 U.S.C. 154(b) by 0 days.

(21) Appl. No.: 10/107,242

(22) Filed: Mar. 28, 2002

(65) Prior Publication Data
US 2002/0155947 A1 Oct. 24, 2002

Related U.S. Application Data

(63) Continuation of application No. 09/535,978, filed on Mar. 27, 2000, now abandoned, which is a continuation of application No. 08/987,132, filed on Dec. 8, 1997, now abandoned.

(30) Foreign Application Priority Data

Dec. 13, 1996 (FR) .............................. 96 15360

(51) Int. Cl.⁷ .................. B01J 27/06; B01J 27/132; B01J 27/128
(52) U.S. Cl. ............. 502/228; 502/305; 502/313; 502/315; 502/224; 502/229
(58) Field of Search ................. 502/305, 313, 502/315, 224, 228, 229

(56) References Cited

U.S. PATENT DOCUMENTS

| | | | |
|---|---|---|---|
| 3,846,340 A | 11/1974 | Okuyama et al. | |
| 4,036,879 A | 7/1977 | Habermann | |
| 4,278,566 A | 7/1981 | Hensley, Jr. et al. | |
| 5,571,770 A | 11/1996 | Kim et al. | ................. 502/307 |

FOREIGN PATENT DOCUMENTS

| | | | |
|---|---|---|---|
| EP | 0 514 932 A2 | 11/1992 | ...................... 19/8 |
| FR | 2 669 022 | 5/1992 | ...................... 19/8 |
| FR | 0 546 883 A1 | 6/1993 | ...................... 23/86 |
| FR | 0 657 408 A1 | 6/1995 | ...................... 17/20 |
| GB | 1 055 346 | 1/1967 | ......................... 1/7 |
| WO | WO 93/25507 | 12/1993 | .................... 17/20 |

OTHER PUBLICATIONS

"Catalysis, Volume II, Fundamental Principles (Part 2)", Edited by Paul H. Emmett, 1955, Chapter 2, pp. 105–109.*

* cited by examiner

*Primary Examiner*—Elizabeth D. Wood
(74) *Attorney, Agent, or Firm*—Smith, Gambrell & Russell, LLP

(57) ABSTRACT

Catalysts which are useful in the fluorination of halogenated hydrocarbons by HF in the gas phase are obtained by simple impregnation of a bulk chromium oxide with a solution of a nickel derivative, the chromium oxide used exhibiting a BET specific surface of greater than 150 m²/g and a pore volume of greater than 0.15 ml/g.

12 Claims, No Drawings

BULK CATALYSTS BASED ON CHROMIUM AND ON NICKEL FOR THE GAS-PHASE FLUORINATION OF HALOGENATED HYDROCARBONS

This is a continuation application of application Ser. No. 09/535,978, filed Mar. 27, 2000, now abandoned, which is a continuation of application Ser. No. 08/987,132, filed Dec. 8, 1997 (abandoned).

The present invention relates to the field of the fluorination of halogenated hydrocarbons and more particularly to the preparation of bulk catalysts based on chromium and on nickel which can be used for this purpose.

One of the various access routes to hydroalkanes, which are substitutes for CFCs (ChloroFluoroCarbons), is gas-phase fluorination with HF. For this, many catalysts are described in the literature and a good number of them are based on chromium. The change from CFCs to the substitutes has led to research into the catalysts in order to improve their performances, both from the viewpoint of activity and of selectivity.

First of all, studies have been carried out in order to improve the performances of chromium-based catalysts. Thus, Patent Application EP 514,932 claims, as fluorination catalyst, a chromium oxide with a high specific surface which, according to the authors, has a high activity and a long lifetime.

In the same way, work has been carried out in order to modify the performances of chromium-based catalysts by addition of doping agents or of cocatalysts. Thus, as regards mixed Ni—Cr catalysts, Patent FR 2,669,022 claims the synthesis of F134a (1,1,1,2-tetrafluoroethane) by gas-phase fluorination of F133a (1-chloro-2,2,2-trifluoroethane) over a catalyst based on derivatives of nickel and of chromium which are supported on more or less fluorinated aluminas, or even on aluminium fluoride. The presence of the support contributes certain characteristics to the catalyst, in particular a degree of strength. On the other hand, there is a risk, with the small amounts of active materials, of limiting the catalytic activity, or even the lifetime of the catalyst; in addition, the low contents of non-precious metals do not facilitate a profitable recovery of the spent catalysts.

Patent EP 546,883 describes the preparation of bulk catalysts based on chromium and on nickel by the sol-gel method in several stages, the first consisting in forming a mixed sol of chromium III and nickel II hydroxides. This technique, which starts with a mixture of the precursors of the chromium and of the nickel, is relatively lengthy and expensive to implement.

In Patent Application WO 93/25507, the preparation of catalysts based on chromium and on at least one derivative of a transition metal chosen from nickel, platinum and palladium is carried in various ways: impregnation of a support, coprecipitation, impregnation of a chromium derivative, and the like. No characteristic of the catalyst or of the support is provided in this document.

It has now been found that a mixed Ni—Cr catalyst which is particularly effective in the gas-phase fluorination by HF of saturated or olefinic halogenated hydrocarbons can be obtained by simple impregnation of a bulk chromium oxide, with a large specific surface and with a high pore volume, with a solution of a nickel derivative.

The subject of the invention is thus bulk catalysts based on chromium and on nickel which are obtained by impregnation of an amorphous chromium III oxide with a solution of a nickel derivative, characterized in that the bulk chromium oxide used exhibits a BET specific surface of greater than 150 $m^2/g$, preferably of greater than 180 $m^2/g$, and a pore volume (defined as the volume of the pores with a radius of less than 7.5 $\mu$m) of greater than 0.15 ml/g, preferably of greater than 0.18 ml/g.

A chromium III oxide with a BET specific surface greater than 150 $m^2/g$ can be synthesized by the various techniques known to the person skilled in the art. Mention may be made, as non-limiting example, of the calcination of a chromium III hydroxide precipitate, the formation of a chromium III hydroxide gel, followed by the calcination thereof, the reduction of chromium VI by an alcohol or another reducing agent, or the thermal decomposition of an oxidized derivative of chromium, such as $CrO_3$ and $(NH_4)_2Cr_2O_7$. It is preferable to use a chromium oxide obtained by calcination of a chromium III hydroxide or by reduction of chromium VI oxide. Commercial chromium III oxides may be suitable, provided that they have a suitable specific surface and a suitable porosity.

Chromium III oxide can be provided in various forms (pellets, extrudates, balls, and the like). The form used very clearly establishes the form of the final catalyst; it must therefore not be detrimentally affected by the impregnation stage. To achieve this, various additives (graphite, crystalline $Cr_2O_3$, and the like) can be added during the shaping operation, in order to improve the strength of the chromium particles.

Chromium III oxide is impregnated by means of an aqueous or alcoholic solution of a nickel precursor which can be a nickel II oxide, hydroxide, halide, oxyhalide, nitrate, sulphate or other compound which is soluble in aqueous or alcoholic medium. The preferred compound is nickel chloride.

The Ni/Cr atomic ratio in the final catalyst can vary between 0.01 and 1, preferably between 0.02 and 0.6. An atomic ratio of between 0.02 and 0.4 is particularly advantageous.

The impregnation of the chromium oxide can be carried out before the catalyst is shaped (impregnation of $Cr_2O_3$ powder) or on chromium III oxide which has already been shaped (balls, pellets, extrudates, and the like). The latter technique is preferred when the form of the catalyst is not detrimentally affected by the impregnation stage. The impregnation can be carried out according to the various techniques known to the person skilled in the art (immersion, impregnation with a volume adjusted to the porosity of the catalyst, and the like). Impregnation adjusted to the pore volume of the catalyst is the preferred technique. The impregnation solution can be an aqueous solution or an alcoholic solution. When there is no solubility problem, the aqueous solution is preferred; the exothermicity due to the reduction by the alcohol of the surface chromium VI (always present at a low content in $Cr_2O3$) is thus avoided.

In order to optimize the activity of the catalyst, it is advisable to subject it to a pretreatment with HF in the absence of organic compounds. As chromium III oxide and the nickel derivatives become fluorinated in the presence of HF, it is necessary to carry out this fluorination while controlling the exothermicity of the reaction, in order to prevent the catalyst from deteriorating (crystallization, deterioration of the balls, pellets or extrudates, and the like). A typical pretreatment (or activation) of the catalyst first comprises a drying stage under an inert gas (nitrogen, helium, or the like) or air at a temperature of between 100 and 350° C., followed by a stage of activation by HF. To control the exothermicity, the HF is, on the one hand, introduced at low temperature (150–200° C.) and, on the other hand, it is diluted in air or, preferably, in an inert gas. After the "exothermicity waves" due to the adsorption of HF on the catalyst have passed, the temperature is gradually increased, in order to reach 350–380° C. and to observe a stationary phase at this temperature. When the strength of the catalyst allows it, the latter can be activated as a stirred or fluidized bed; control of exothermicity is thus easier. In order to avoid any deterioration in the catalyst, it is recommended that a temperature of 400° C. should not be exceeded.

Another subject of the invention is the use of these bulk catalysts for the catalytic fluorination of saturated or olefinic halogenated hydrocarbons by HF in the gas phase.

The halogenated hydrocarbons capable of resulting in HCFCs (HydroChloroFluoroCarbons) or in HFCs (HydroFluoroCarbons) by gas-phase fluorination are compounds containing one or more carbon atoms which result in final products, or even in synthetic intermediates, containing one or more hydrogen atoms. Mention may be made, as non-limiting examples, in this category, of the following compounds: $CH_2Cl_2$, $CH_2ClF$, $CHCl_3$, $CCl_2=CHCl$, $CCl_2=CCl_2$, $CH_2Cl—CF_3$, $CHCl_2—CF_3$, $CHClF—CF_3$, $CH_3—CCl_3$, $CH_3—CCl_2F$, $CH_3—CClF_2$, $C_3F_6$, $CCl_3—CH_2—CHCl_2$, $CF_3—CH=CHCl$, $CF_3—CH_2—CHClF$, $CH_3—CCl_2—CH_3$, $CCl_3—CF_2—CHCl_2$, $CCl_3—CF_2—CH_2Cl$, $CCl_3—CF_2—CH_3$, $CHCl_2—CHCl—CH_3$, $CH_2Cl—CHCl—CH_3$, and the like.

The fluorination temperature depends on the starting halogenated hydrocarbon and, very clearly, on the desired reaction products. It is generally between 50 and 500° C. but it is often preferable to carry out the fluorination at a temperature of between 100 and 450° C. and more particularly between 120 and 400° C.

The contact time also depends on the starting material and the desired products. It is generally between 3 and 100 seconds. A good compromise between a high degree of conversion and a high productivity very often lays down a contact time of less than 30 seconds.

The molar ratio: HF/organic reactant(s) is also related to the nature of the starting material and depends, inter alia, on the stoichiometry of the reaction. In the majority of cases, it can vary between 1/1 and 30/1. However, in order to obtain high productivities, it is advantageously less than 20.

The working pressure is not critical but is generally between 0.08 and 2 MPa absolute and, preferably, between 0.1 and 1.5 MPa absolute.

The catalysts can operate as a stationary bed but also, when they allow this, as a fluid or stirred bed.

When the fluorination reaction results in fouling of the catalyst (formation of "coke"), it is possible to carry out the fluorination by continuously injecting an oxidizing agent (air, oxygen, or the like). When the catalyst is deactivated by coking, it is also possible to regenerate by a treatment with air or with oxygen or by a $Cl_2/HF$ mixture, at a temperature of between 250 and 400° C.

The following examples illustrate the invention without limiting it.

PREPARATION OF THE CATALYSTS

EXAMPLE 1

Catalyst A 100 ml (139 g) of a commercial chromium III oxide in the form of pellets exhibiting the following characteristics:

| | |
|---|---|
| BET specific surface (m²/g) | 223 |
| Pore volume (r < 7.5 μM) | 0.272 ml/g |
| graphite (pelleting binder) | 4.1 weight % | are impregnated at room temperature and atmospheric pressure with a nickel chloride solution composed of 22.6 g of $NiCl_2.6H_2O$ in 20 ml of water.

At the end of impregnation, all the solution is absorbed by the catalyst. The latter is then dried at room temperature and at atmospheric temperature.

This impregnated catalyst is then dried under nitrogen at 200° C. for 18 hours and then a portion (70 ml) is activated with a nitrogen/HF mixture, the temperature being controlled so as not to exceed an exothermicity of 30° C. with respect to the set temperature. The mixture is gradually enriched in HF and the temperature gradually increased to reach 380° C. under pure HF (1 mol/h of HF). Finally, the catalyst is pretreated with pure HF under these operating conditions for 18 hours.

The catalyst, thus impregnated, dried and activated, contains 3.5% by mass of nickel.

EXAMPLE 2

Catalyst B 100 ml of the chromium III oxide described in Example 1 are immersed at room temperature in an aqueous nickel chloride solution prepared by dissolving 75 g of $NiCl_2.6H_2O$ in 35 ml of water. The catalyst is then dried and then activated according to the procedure of Example 1.

The catalyst, thus impregnated, dried and activated, contains 4.2% by mass of nickel.

EXAMPLE 3

Catalyst C

This catalyst is prepared, dried and activated according to the procedure of Example 1, except that the impregnation solution is composed of 34 g of $NiCl_2.6H_2O$ and 18 ml of water.

After drying and activation, the catalyst, thus impregnated, contains 5.1% by mass of nickel.

Comparative Example 4

Nickel-free Catalyst D

The chromium III oxide described in Example 1 is used directly without being subjected to impregnation by nickel.

Before the fluorination test, the catalyst is subjected to an N₂/HF pretreatment comparable to that described in Example 1.

Comparative Example 5

Catalyst E Prepared From a Chromium Oxide Which Does Not Observe the Specific Surface and Porosity Criteria 100 ml of a commercial chromium oxide in the powder form, exhibiting the following characteristics:

| BET specific surface (m²/g) | 66 |
|---|---|
| Pore volume (r < 7.5 μm) | 0.14 ml/g | are impregnated by immersion in an aqueous nickel chloride solution consisting of 75 g of NiCl₂.6H₂O and 35 ml of water. The catalyst is then dried and then activated according to the procedure of Example 1.

After drying and activation, the catalyst, thus impregnated, contains 3.6% by mass of nickel.

Fluorination Examples

The catalysts described in Examples 1 to 5 were used in the gas-phase fluorination of perchloroethylene (Examples 6 to 11) and of 1-chloro-2,2,2-trifluoroethane (Examples 12 and 13).

The operating conditions and the results obtained are combined in the following Tables I and II, where the abbreviations have the following meanings:

| F114 + F114a | dichlorotetrafluoroethanes |
|---|---|
| F115 | chloropentafluoroethane |
| F122 | 1,1-difluoro-1,2,2-trichloroethane |
| F123 | 1,1-dichloro-2,2,2-trifluoroethane |
| F123a | 1,2-dichloro-1,1,2,-trifluoroethane |
| F124 | 1-chloro-1,2,2,2-tetrafluoroethane |
| F124a | 1-chloro-1,1,2,2-tetrafluoroethane |
| F125 | pentafluoroethane |
| F143a | 1,1,1-trifluoroethane |
| F1111 | fluorotrichloroethylene |
| F1122 | 1-chloro-2,2-difluoroethylene |

The examples 6 to 9, carried out with the catalysts A, B and C according to the invention, show that these catalysts, which are easy to prepare (simple impregnation of a commercial chromium oxide), are very good fluorination catalysts; moreover, the recovery of these spent catalysts is profitable on account of the chromium contents.

The tests of Example 10, which are carried out with the catalyst D, reflect, in comparison with the results obtained with the catalysts A, B and C, the beneficial effect of nickel.

Finally, the tests of Example 11, which are carried out with the catalyst E, show that a catalyst prepared with a chromium oxide which does not observe the specific surface and pore volume criteria defined in the present invention gives markedly poorer fluorination results.

TABLE I

Fluorination of perchoroethylene

| EXAMPLE | 6 | | 7 | 8 | 9 | | 10, Comparative | | 11, Comparative | |
|---|---|---|---|---|---|---|---|---|---|---|
| OPERATING CONDITIONS | | | | | | | | | | |
| Catalyst | A | A | A | A | B | C | D | D | E | E |
| Temperature (° C.) | 300 | 350 | 280 | 280 | 280 | 300 | 350 | 300 | 300 | 350 |
| Molar ratio: HF/C₂Cl₄ | 7.1 | 7.1 | 7.2 | 6.8 | 6.9 | 6.9 | 6.1 | 7.0 | 7.3 | 7.1 |
| Molar ratio: Oxygen/C₂Cl₄ | 0.01 | 0.01 | 0.01 | 0.01 | 0.01 | 0.01 | 0.01 | 0.01 | 0.01 | 0.01 |
| Pressure (MPa) | 0.1 | 0.1 | 0.1 | 0.1 | 0.1 | 0.1 | 0.1 | 0.1 | 0.1 | 0.1 |
| Contact time (seconds) | 5.2 | 4.9 | 5.4 | 5.4 | 5.5 | 5.3 | 5.5 | 5.1 | 5.3 | 5.4 |
| Age of the catalyst (hours) | 24 | 48 | 48 | 448 | 44 | 24 | 24 | 48 | 24 | 48 |
| RESULTS | | | | | | | | | | |
| Overall degree of conversion of C₂Cl₄ (%) | 72.3 | 82.6 | 66.7 | 62.6 | 65.2 | 69.3 | 91.2 | 72.8 | 53.8 | 60.6 |
| Selectivity (molar %) for: | | | | | | | | | | |
| F125 | 22.2 | 49.8 | 10.3 | 8.9 | 9.1 | 19.8 | 25.0 | 15.3 | 4.3 | 7.4 |
| F124 | 32.3 | 16.7 | 31.3 | 34.6 | 29.0 | 32.5 | 11.6 | 32.3 | 23.1 | 30.6 |
| F124a | 1.5 | 0.7 | 1.4 | 1.9 | 1.5 | 1.5 | 0.2 | 1.5 | 1.4 | 1.7 |
| F123 | 30.5 | 13.5 | 42.0 | 37.7 | 44.5 | 32.3 | 22.0 | 36.1 | 47.2 | 37.4 |
| F123a | 1.9 | 0.5 | 2.8 | 2.9 | 2.4 | 1.9 | 0.1 | 1.7 | 4.6 | 1.9 |
| F122 | 3 | 0.7 | 5.4 | 5.5 | 6.2 | 3.6 | 0 | 2.5 | 10 | 5.6 |
| F133a | 0.6 | 4.8 | 0.4 | 0.2 | 0.3 | 0.6 | 11.1 | 2.5 | 0.4 | 3.5 |
| F155 | 0.5 | 5.3 | 0.2 | 0.1 | 0.1 | 0.7 | 21.3 | 2.1 | 0.5 | 4.8 |
| F114 + F114a | 2.2 | 3.1 | 1.8 | 1.2 | 1.6 | 2.1 | 7.0 | 3.0 | 1.6 | 3.1 |
| F1111 | 4.6 | 4.1 | 4.2 | 6.5 | 5.0 | 4.9 | 0.9 | 2.9 | 6.5 | 3.1 |
| Others | 0.7 | 0.8 | 0.2 | 0.5 | 0.3 | 0.1 | 0.6 | 0.1 | 0.4 | 0.9 |

TABLE II

Fluorination of F133a

| EXAMPLE | 12, Comparative | 13 |
|---|---|---|
| OPERATING CONDITIONS | | |
| Catalyst | D | A |
| Temperature (° C.) | 350 | 350 |

TABLE II-continued

Fluorination of F133a

| EXAMPLE | 12, Comparative | 13 |
|---|---|---|
| Pressure (MPa) | 1.5 | 1.5 |
| Molar ratio: HF/F133a | 2.0 | 2.0 |
| Molar ratio: Oxygen/F133a | 0.01 | 0.01 |
| Contact time (seconds) | 21.8 | 22.1 |
| Age of the catalyst (hours) | 23 | 24 |
| RESULTS | | |
| Overall degree of conversion of F133a (%) | 15.5 | 15.4 |
| Selectivity (molar %) for: | | |
| F134a | 90.8 | 96.1 |
| F1122 | 0.2 | 0.1 |
| F123 | 1.2 | 0.6 |
| F124 | 1.3 | 0.8 |
| F125 | 0.7 | 0.4 |
| F143a | 0.4 | 0.1 |
| Others (CO, $CO_2$, $CHF_3$, and the like) | 5.4 | 1.9 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A bulk catalyst comprising chromium and nickel, obtained by impregnation of an amorphous chromium III oxide with a solution of a nickel compound,
   wherein the chromium oxide used exhibits a BET specific surface of greater than 150 $m^2/g$ and a pore volume of greater than 0.15 ml/g,
   wherein the catalyst is dried under an inert gas or under air at a temperature of between 100 and 350° C. and then activated with HF, and
   wherein the HF is first introduced diluted in air or, optionally, in an inert gas at a temperature ranging from 150 to 200° C. and then pure HF at a temperature of less than 400° C.;
   further wherein the Ni/Cr atomic ratio is between 0.02 and 0.4:1.

2. The catalyst according to claim 1, wherein the catalyst is obtained from a chromium oxide having a BET specific surface of greater than 180 $m^2/g$.

3. The catalyst according to claim 1, wherein the catalyst is obtained from a chromium oxide exhibiting a pore volume of greater than 0.18 ml/g.

4. The catalyst according to claim 1, wherein the chromium oxide used originates from the calcination of a chromium III hydroxide precipitate or from the reduction of chromium VI oxide.

5. The catalyst according to claim 1, wherein the nickel compound is a nickel II oxide, hydroxide, halide, oxyhalide, nitrate or sulphate.

6. The catalyst according to claim 1, wherein the Ni/Cr atomic ratio is between 0.05:1 and 0.4:1.

7. The catalyst according to claim 1, wherein the catalyst is obtained from an aqueous or alcoholic solution of a nickel compound.

8. Catalyst according to claim 5, wherein the nickel compound is nickel chloride.

9. A bulk catalyst comprising chromium and nickel, obtained by impregnation of an amorphous chromium III oxide with a solution of a nickel compound,
   wherein the chromium oxide used exhibits a BET specific surface of greater than 150 $m^2/g$ and a pore volume of greater than 0.15 ml/g,
   wherein the nickel compound is nickel nitrate or nickel sulphate,
   wherein the catalyst is dried under an inert gas or under air at a temperature of between 100 and 350° C. and then activated with HF, and
   wherein the HF is first introduced diluted in air or, optionally, in an inert gas at a temperature ranging from 150 to 200° C. and then pure HF at a temperature of less than 400° C.;
   further wherein the Ni/Cr atomic ratio is between 0.02 and 0.4:1.

10. A bulk catalyst comprising chromium and nickel, obtained by impregnation of an amorphous chromium III oxide with a solution of a nickel compound,
    wherein the chromium oxide exhibits a BET specific surface of greater than 150 $m^2/g$ and a pore volume of greater than 0.15 ml/g,
    wherein the Ni/Cr atomic ratio is between 0.02 and 0.4,
    wherein the catalyst is dried under an inert gas or under air at a temperature of between 100 and 350° C. and then activated with HF, and
    wherein the HF is first introduced diluted in air or, optionally, in an inert gas at a temperature ranging from 150 to 200° C. and then pure HF at a temperature of less than 400° C.

11. A bulk catalyst comprising chromium and nickel, obtained by impregnation of an amorphous chromium III oxide with a solution of a nickel compound,
    wherein the chromium oxide used exhibits a BET specific surface of greater than 150 $m^2/g$ and a pore volume of greater than 0.15 ml/g,
    wherein the Ni/Cr atomic is between 0.02 and 0.4,
    wherein the nickel compound is nickel nitrate or nickel sulphate,
    wherein the catalyst is dried under an inert gas or under air at a temperature of between 100 and 350° C. and then activated with HF, and
    wherein the HF is first introduced diluted in air or, optionally, in an inert gas at a temperature ranging from 150 to 200° C. and then pure HF at a temperature of less than 400° C.

12. A bulk catalyst comprising chromium and nickel, obtained by impregnation of an amorphous chromium III oxide with a solution of a nickel compound,
    wherein the chromium oxide exhibits a BET specific surface of greater than 150 $m^2/g$ and a pore volume of greater than 0.15 ml/g,
    further wherein the Ni/Cr atomic ratio is between 0.02 and 0.4.

* * * * *